United States Patent [19]

Tuong et al.

[11] Patent Number: 4,514,317

[45] Date of Patent: Apr. 30, 1985

[54] ANISOTROPIC COMPOUNDS AND LIQUID CRYSTAL MIXTURES

[75] Inventors: Huynh-Ba Tuong, Baden; Stephen M. Kelly, Oberrohrdorf; Maged A. Osman, Zurich, all of Switzerland

[73] Assignee: Merck Patent Gesellschaft mit beschrankter Haftung, Darmstadt, Fed. Rep. of Germany

[21] Appl. No.: 460,943

[22] Filed: Jan. 25, 1983

[30] Foreign Application Priority Data

Feb. 4, 1982 [CH] Switzerland ............................ 675/82

[51] Int. Cl.$^3$ .......................... C09K 3/34; G02F 1/13; C07C 121/64
[52] U.S. Cl. .......................... 252/299.62; 252/299.63; 252/299.64; 252/299.5; 350/350 R; 350/350 S; 260/465 C; 260/465 D; 260/465 F; 260/465 G; 260/465 H
[58] Field of Search ...................... 252/299.62, 299.63, 252/299.64, 299.65, 299.67, 299.5, 299.66; 350/350 R, 350 S; 260/465 C, 465 D, 465 F, 465 G, 465 H

[56] References Cited

U.S. PATENT DOCUMENTS

| | | | |
|---|---|---|---|
| 4,219,256 | 8/1980 | Gray et al. | 252/299.62 |
| 4,229,315 | 10/1980 | Krause et al. | 252/299.63 |
| 4,237,026 | 12/1980 | Eidenschink et al. | 252/299.63 |
| 4,261,652 | 4/1981 | Gray et al. | 252/299.62 |
| 4,279,770 | 7/1981 | Inukai et al. | 252/299.62 |
| 4,357,678 | 11/1982 | Carr et al. | 252/299.63 |
| 4,368,135 | 1/1983 | Osman | 252/299.63 |
| 4,400,061 | 8/1983 | Carr et al. | 252/299.63 |
| 4,400,293 | 8/1983 | Romer et al. | 252/299.5 |
| 4,439,015 | 3/1984 | Rich et al. | 252/299.62 |
| 4,479,885 | 10/1984 | Mukoh et al. | 252/299.62 |

FOREIGN PATENT DOCUMENTS

| | | | |
|---|---|---|---|
| 19665 | 12/1980 | European Pat. Off. | 252/299.63 |
| 56501 | 12/1981 | European Pat. Off. | 252/299.61 |
| 72204 | 2/1983 | European Pat. Off. | 252/299.62 |
| 84194 | 7/1983 | European Pat. Off. | 252/299.61 |
| 2931637 | 12/1980 | Fed. Rep. of Germany | 252/299.63 |
| 2933563 | 2/1981 | Fed. Rep. of Germany | 252/299.63 |
| 2939782 | 4/1981 | Fed. Rep. of Germany | 252/299.64 |
| 3237367 | 4/1983 | Fed. Rep. of Germany | 252/299.63 |
| 3205766 | 8/1983 | Fed. Rep. of Germany | 252/299.63 |
| 55-66556 | 5/1980 | Japan | 252/299.63 |
| WO82/00654 | 3/1982 | World Intel. Prop. Org. | 252/299.63 |
| 2027027 | 2/1980 | United Kingdom | 252/299.63 |
| 2078727 | 1/1982 | United Kingdom | 252/299.63 |
| 2093057 | 8/1982 | United Kingdom | 252/299.62 |

OTHER PUBLICATIONS

Gray; G. W. et al., Mol. Cryst. Liq. Cryst., vol. 75, pp. 95–108, (1981), vol. 63, pp. 3–18, (1981).

*Primary Examiner*—Teddy S. Gron
*Attorney, Agent, or Firm*—Oblon, Fisher, Spivak, McClelland & Maier

[57] ABSTRACT

Anisotropic compounds having negative DC anisotropy and improved photochemical stability have the formula (1) given in patent claim 1; none of the benzene rings present in the molecule (1) is bonded directly to two oxygen atoms, as a result of which quinoidal bonding states which reduce the photochemical stability of anisotropic compounds in the case of benzene rings with two lateral nitrile groups are excluded.

4 Claims, No Drawings

ANISOTROPIC COMPOUNDS AND LIQUID CRYSTAL MIXTURES

The invention relates to novel anisotropic compounds having a negative DC anisotropy, and liquid crystal mixtures (LC mixtures) which contain these compounds as components.

It is known that nematic LC mixtures having a very negative value of Δε (i.e. a negative value of not less than 2), Δε being the DC anisotropy or DCA, are required for various types of electrooptical displays, for example for so-called "guest/host displays" (GHD) and homeotropic nematic displays (HND).

However, in addition to having a negative DCA, the LC mixtures or components thereof must also have a number of other characteristics, which include, in particular, a high stability in a photochemical, general chemical and electrochemical respect and as low as possible a viscosity, low optical anisotropy (low double refraction tendency) and such properties.

The known compounds having a negative DCA fulfil these requirements only to an inadequate degree; thus, the compounds described by J. C. Dubois et al in Mol. Cryst. Liqu. Cryst. 42 (1977) 139 and in German Offenlegungsschriften Nos. 2,835,662, 2,836,086, 2,613,293 and 2,240,864 and in Soviet Union Pat. No. 562,547 have an ester structure which is built up from two or three aromatic rings and has 1 to 4 laterally bonded groups, such as nitrile groups; these compounds have a comparatively high viscosity and optical anisotropy, and in some cases their DCA values are not sufficiently negative.

To reduce these disadvantages, anisotropic compounds which have a negative DCA and in which the viscosity is decreased by using trans-cyclohexane rings or by using other bridge groups as carboxyl groups in the base structure and the negative DCA can be controlled by using two lateral nitrile groups on one phenyl ring of the structure, the clear point being reduced by these lateral substituents, have been disclosed or proposed in European Offenlegungsschrift No. 0,023,728, filed by the applicant company, and in British Pat. No. 2,027,708 and German Offenlegungsschrift No. 2,931,637.

The only nematic LC mixtures having a relatively highly negative DCA (Δε≈−5) which are at present commercially available are the products from Messrs. Chisso Corp. which have the type names "EN 18" or "EN 24" and are based on the 2,3-dicyanophenol derivatives known from German Offenlegungsschrift No. 2,937,700, i.e. compounds of the formulae

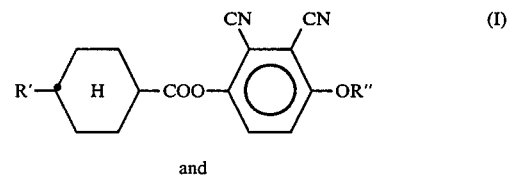

and

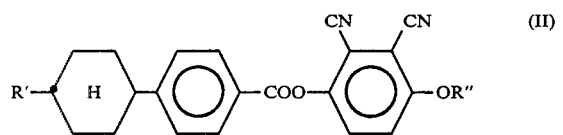

in which R' and R" are alkyl groups. It has been found that the photochemical stability of these compounds is inadequate (cf. Table I from Example 5), which manifests itself by an increase in the conductivity of the LC mixtures under the action of daylight-UV and thus by an adverse increase in the current uptake of displays operating with such LC mixtures.

The object of the invention is to provide novel and improved anisotropic compounds having a negative DCA, an increased photochemical stability and higher clear points. The object of the invention also includes providing LC mixtures having an overall negative DCA and an improved photochemical stability, which are suitable for LC displays which, like the abovementioned GHD and HND systems, require nematic LC mixtures having a high negative DCA.

According to the invention, this object is achieved by novel anisotropic compounds of the formula (1) given in claim 1. Preferred compounds according to the invention have the formulae (2) to (9) given in claims 2 to 9.

Like the abovementioned known compounds of the formulae (I) and (II), all the compounds of the formulae (1) to (9) according to the invention contain the 2,3-dicyanophenyl ring, and accordingly have negative DCA values; however, it has now been found that the inadequate photochemical stability of the known compounds of the formulae (I) and (II) is caused by their common structural element, i.e. the nucleus of the formula (A)

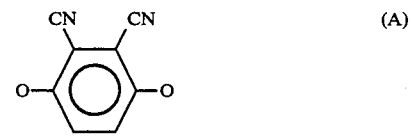

and is probably based on the tendency of this nucleus to form quinoidal or quinoid-like bonding states (B)

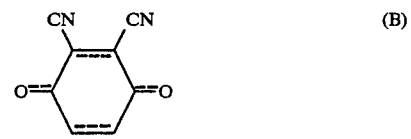

According to the invention, the novel compounds of the formula (1) fulfil the condition that none of the nitrile-substituted benzene rings present in the molecule is bonded directly to two oxygen atoms, so that quinoidal bonding or charge distribution states of the 2,3-dicyanophenyl portion always present or of any other nitrile-substituted benzene rings which may be present are excluded.

Compounds (1) according to the invention can be dinuclear or trinuclear. The dinuclear compounds have the form defined in formula (2) of claim 2, i.e. the compound (2) according to the invention consists of the 2,3-dicyanophenyl nucleus and a bicyclo(2,2,2)octane ring bonded to this via the bridge member $Z^1$ (covalent bond or one of the groups —CH$_2$O—, —CH$_2$CH$_2$—, —COO—, optionally either in the form shown or in the corresponding reverse form, i.e. —OCH$_2$—or —OOC—).

Preferred dinuclear and preferred trinuclear structures contain the end group $R^3$ having the meaning given in claim 1, $R^3$=H usually being less preferable. The preferred dinuclear and trinuclear compounds of the formulae (2) to (9), as defined in claims 2 to 9, according to the invention furthermore contain another end group, which has one of the meanings given for $R^3$.

The trinuclear compounds contain at least one bicyclo(2,2,2)octane ring

(i.e. if n in formula (1) is one), and can contain two if n in formula (1) is zero and $R^1$ or $R^2$ is the cyclic radical of the formula (1c).

The use of bicyclo(2,2,2)octane rings in dinuclear or trinuclear anisotropic compounds having a positive DCA is known, for example, from British Pat. No. 2,027,027. In contrast, no anisotropic compounds having a negative DCA and containing one or two bicyclo(2,2,2)-octane ring(s) as a structural element have yet been disclosed, and it was in no way obvious that combination of a 2,3-dicyanophenyl ring with at least one bicyclo(2,2,2)octane ring would be particularly advantageous for anisotropic compounds having a negative DCA. This is, however, the case; as was found in the investigations which were carried out by the applicant company and which led to the invention, the lowering of the clear point of the known compounds having a negative DCA which was generally caused by the two lateral nitrile groups on the 2,3-dicyanophenyl ring could hitherto only be compensated by structural elements which increased the viscosity for example by lengthening the molecule; surprisingly, the present novel compounds (1) having a negative DCA provide not only which is improved photochemical stability in comparison with the prior art, but also a comparatively smaller reduction in clear point by the lateral nitrile groups.

If n in formula (1) is the value zero, one of the end groups $R^1$ or $R^2$ can be a cyclic radical of the formulae (1a), (1b) or (1c) given in claim 1; the definition of $R^3$ corresponds to the non-cyclic meanings of $R^1$ and $R^2$; the bridge $Z^2$ has one of the meanings given for $Z^1$; $Z^3$ is also a bridge, and in particular either a covalent bond or one of the groups —CH$_2$CH$_2$— or —COO— (or —OOC—).

The definition of $X^1$ and $X^2$ in formula (1) and of $X^3$ and $X^4$ in formula (1a) also includes halogen atoms (F, Cl, Br and iodine) and the nitrile group, in addition to hydrogen. Compounds according to the invention thus contain at least the two lateral nitrile groups, shown in formula (1), on the benzene ring always present, but may contain one or two additional lateral substituents of the type mentioned (halogen or nitrile) in the second benzene ring which may be present (i.e. if either n is one or one of the radicals $R^1$ or $R^2$ is the cyclic radical (1a)).

If n in formula (1) is one, both the radicals $R^1$ and $R^2$ are hydrogen or alkyl, alkoxy, alkanoyloxy or alkoxycarbonyl groups with in each case 1 to 12 carbon atoms in the alkyl part in a straight or branched chain, which may be chiral; if n in formula (1) is zero—as explained above—either $R^1$ or $R^2$ can be a radical of the formulae (1a), (1b) or (1c), in which $R^3$ has the non-cyclic meaning of $R^1$ or $R^2$ just mentioned. $R^4$ in the formulae (2) to (9) has one of the meanings given for $R^3$.

The compounds according to the invention can be prepared by various synthesis routes such as are known per se for the preparation of known anisotropic compounds containing at least one bicyclo(2,2,2)octane ring and at least one benzene ring. For example, a corresponding bicyclo(2,2,2)octane compound is reacted with a 2,3-dicyanophenyl compound; alternatively, corresponding bicyclo(2,2,2)octane-phenyl compounds can be halogenated, in order to introduce halogen atoms in the 2,3-position of the benzene ring, and the corresponding bicyclo(2,2,2)octane-2,3-dihalogenophenyl compound can be converted into the corresponding 2,3-dicyano compound. Typical general examples are illustrated in the following equations, in which "Ts" is the tosyl group and the other symbols have the meanings given above:

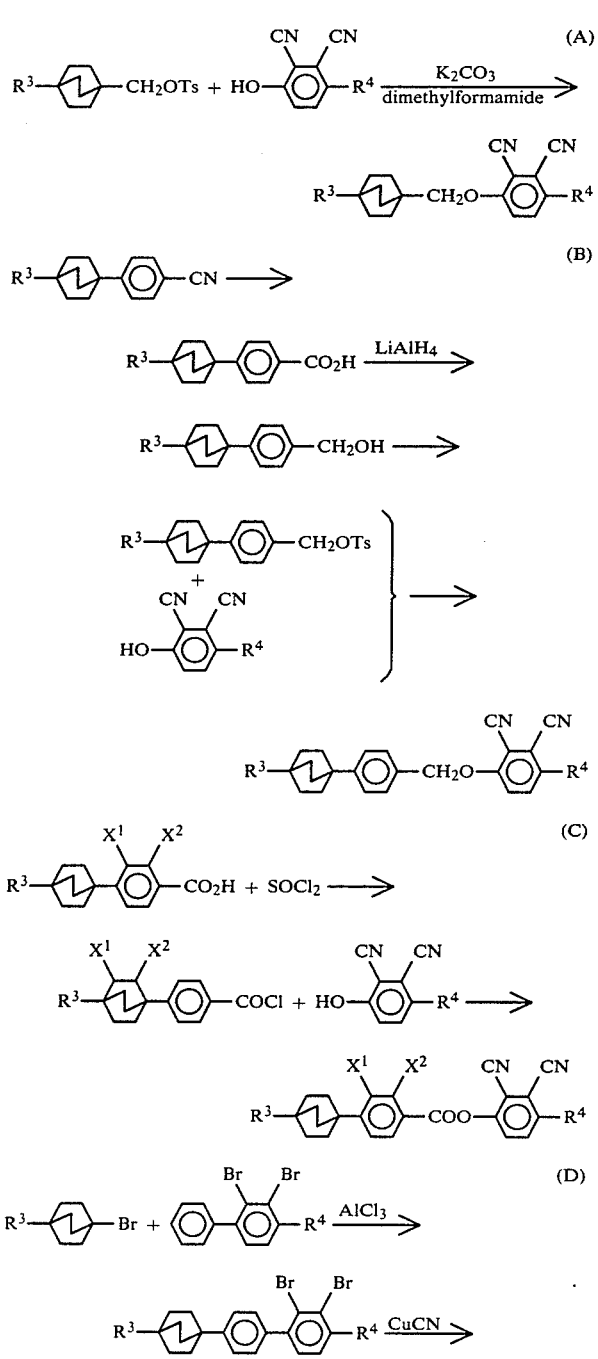

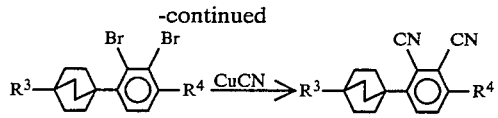

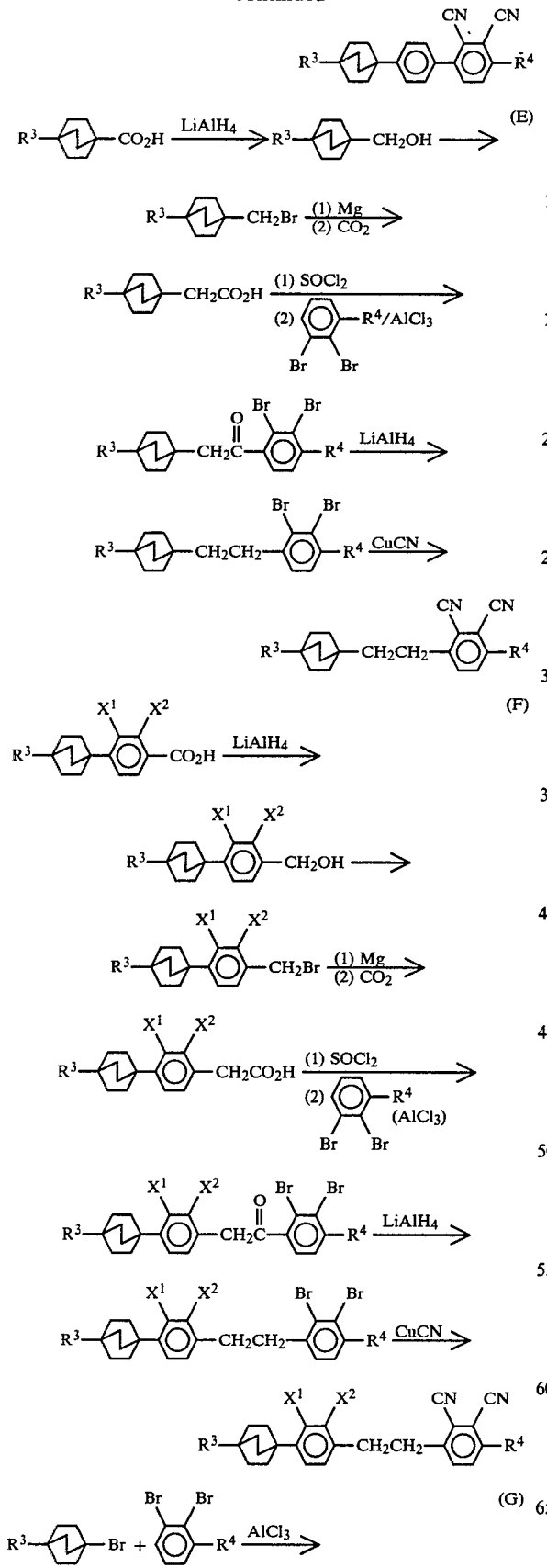

Suitable starting compounds for the reactions according to the above equations are known from the literature, or they can be prepared analogously to known compounds. Starting compounds with bicyclo(2,2,2)octane groups and their preparation can be found, in particular, in the published British Patent Applications Nos. 78/32,350, 78/32,351, 80/05,351 and 81/02,382.

The invention is illustrated in more detail with the aid of the following examples.

EXAMPLE 1

Preparation of 2,3-dicyano-4-pentylphenyl 4-pentylbicyclo(2,2,2)octane-1-carboxylate 25 mmoles of 4-pentylbicyclo(2,2,2)octane-1-carboxylic acid are warmed to the reflux temperature with 40 ml of thionyl chloride for 30 minutes. The acid chloride formed was freed from excess thionyl chloride. The acid chloride thus obtained was now added dropwise to a solution of 25 mmoles of 2,3-dicyano-4-pentylphenol (m.p. 142° C.) in 100 ml of pyridine at 80° C. When the reaction had ended, the mixture was poured into excess dilute hydrochloric acid and extracted with methylene chloride. The crude product obtained from the extract by evaporation was recrystallized. The resulting title compound of this example is monotropically nematic (K 84.0 N (36.1) I) and has a negative DCA.

EXAMPLE 2

Preparation of 2,3-dicyano-4-pentylphenyl 4-(4-pentyl-1-bicyclo(2,2,2)octyl)-benzoate 36.5 mmoles of 4-(4-pentyl-1-bicyclo(2,2,2)-octyl)-benzoic acid were refluxed with 50 ml of thionyl chloride for 1 hour. The excess thionyl chloride was distilled off. The resulting acid chloride was added dropwise to a solution of 36.5 mmoles of 2,3-dicyano-4-pentylphenol in 100 ml of pyridine. The reaction mixture was stirred at 80° C. until the reaction had ended and was then poured onto dilute hydrochloric acid. The product was extracted with methylene chloride. For purification, the product was recrystallized. It displays an enantiotropic nematic phase (K 130.9 N (137.9) I) and has a negative DCA.

EXAMPLE 3

Preparation of 4-propyl-1-bicyclo(2,2,2)octylmethyl 2,3-dicyano-4-pentylphenyl ether 50 ml of dimethylformamide were added to 0.04 mole of 2,3-dicyano-4-pentylphenol, 0.2 mole of potassium carbonate and 0.04 mole of 4-propyl-1-bicyclo(2,2,2)-octylmethyl bromide. The mixture was stirred at 80° C. for 48 hours. The mixture was then cooled to room temperature and poured into 200 ml of water and the organic phase was extracted. The organic extract was washed with water and dried over magnesium sulfate. After the solvent had been evaporated off, the crude product was recrystallized several times. The pure product has a high melting point of 133.1° C. and a negative DCA.

EXAMPLE 4

Preparation of 2,3-dicyano-4-pentylphenyl 4-heptylbicyclo(2,2,2)octane-1-carboxylate This compound was prepared analogously to Example 1, but using the corresponding 4-heptyl-bicyclo(2,2,2)-octane-1-carboxylic acid. The resulting compound is monotropically nematic (K 90 N (49) I) and has a negative DCA.

EXAMPLE 5

To test for photochemical stability, the following compounds or mixtures were exposed to a sunlight lamp (1,500 watts) under identical conditions and were investigated for changes in their electrical conductivity:

Carrier compound

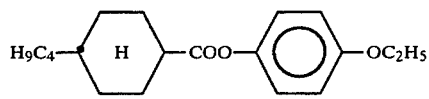

(A)

Carrier compound

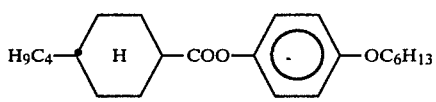

(B)

Comparison compound having a negative DCA

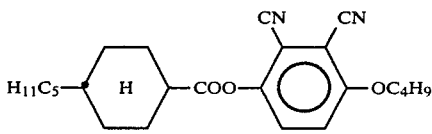

(53)

Compound according to the invention having a negative DCA

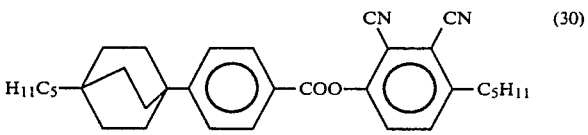

(30)

and a commercial LC mixture from Messrs. Chisso Corp., type EN 24, having a negative DCA. The results are summarized in the following Table I.

TABLE I

| | Conductivity values (μS) measured on: | | | | |
|---|---|---|---|---|---|
| Duration of irradiation with a sunlight lamp of 1,500 watts (hours) | Carrier (A) | Carrier (B) | Mixture of 10 mole % of compound (30) according to the invention and 90 mole % of (A) | Mixture of 11 mole % of comparison compound (53) and 89 mole % of (B) | Commercial mixture "EN 24" |
| 0   | 0.19 | 0.03 | 0.82 | 0.07 | 0.2 |
| 10  | 0.20 | 0.03 | 0.83 | 0.09 | 0.4 |
| 20  | 0.20 | 0.03 | 0.84 | 0.12 | 0.7 |
| 40  | 0.20 | 0.03 | 0.85 | 0.17 | 1.1 |
| 60  | 0.20 | 0.03 | 0.87 | 0.22 | 1.6 |
| 80  | 0.20 | 0.03 | 0.88 | 0.27 | 2.0 |
| 100 | 0.20 | 0.03 | 0.90 | 0.32 | 2.5 |

The values in Table I initially show that the anisotropic compounds (A) and (B) without lateral nitrile groups which are used as carrier compounds in the measurements are photochemically stable even when the phenyl radical is linked directly with two oxygen bonds; although quinoidal bonding states structurally cannot be excluded in (A) and (B), without the lateral nitrile groups this does obviously not lead to photochemical instability.

Compound (53) which is not according to the invention and has a 2,3-dicyanophenyl nucleus which is bonded directly to two oxygen atoms proves to be photochemically unstable, as did the commercial mixture EN 24, since the conductivity value had risen to 4.5 times and, respectively, 12 times the starting value after 100 hours irradiation, whilst the mixture containing the compound according to the invention having a negative DCA displayed only a slightly higher, i.e. only about 10% higher, conductivity after 100 hours irradiation.

In principle, the novel compounds (1) according to the invention having a negative DCA can, like, for example, the anisotropic 2,3-dicyano compounds having a negative DCA which are known from German Offenlegungsschrift No. 2,937,700, be used for LC mixtures having an overall negative DCA, but with the advantage of a substantially higher photochemical stability, and especially together with, for example, the addition, known for the operation of GHD or HND, of other anisotropic compounds, dyes, optically active additives and the like.

In general, the anisotropic compounds according to the invention can make up a substantial or even predominant part of LC mixtures having an overall negative DCA, for example a proportion of the mixture of up to about 60 mole % of compounds of the formula (1). Several different compounds (1), for example in proportions of in each case 1 to 30 mole %, based on the mixture, are in most cases preferably used.

Other compounds of the formula (1) are the following: 2,3-dicyano-4-propylphenyl 4-propylbicyclo(2,2,-2)octane-1-carboxylate, 2,3-dicyano-4-pentylphenyl 4-propylbicyclo(2,2,2)octane-1-carboxylate, 2,3-dicyano-4-pentylphenyl 4-pentylbicyclo(2,2,2)octane-1-carboxylate, 2,3-dicyano-4-propylphenyl 4-heptylbicyclo(2,2,2)octane-1-carboxylate, 2,3-dicyano-4-pentylphenyl 4-heptylbicyclo(2,2,2)octane-1-carboxylate, 2,3-dicyano-4-propylphenyl 4-(4-propyl-1-bicyclo(2,2,2)octyl)-benzoate, 2,3-dicyano-4-pentylphenyl 4-(4-propyl-1-bicyclo(2,2,2)octyl)-benzoate, 2,3-dicyano-4-propylphenyl 4-(4-pentyl-1-bicyclo(2,2,2)octyl)-benzoate, 2,3-dicyano-4-pentylphenyl 4-(4-pentyl-1-bicyclo(2,2,2)octyl)-benzoate, 1-(4-propyl-1-bicyclo(2,2,2)octyl)-2-(2,3-dicyano-4-propyl phenyl)-ethane, 1-(4-propyl-1-bicyclo(2,2,2)octyl)-2-(2,3-dicyano-4-pentylphenyl)-ethane, 1-(4-pentyl-1-bicyclo(2,2,2)octyl)-2-(2,3-dicyano-4-pentylphenyl)ethane, 1-(4-propyl-1-bicyclo(2,2,2)octyl)-2-(2,3-dicyano-4-ethoxyphenyl)-ethane, 1-(4-propyl-1-bicyclo(2,2,2)-octyl)-2-(2,3-dicyano-4-butoxyphenyl)-ethane, 1-(4-pentyl-1-bicyclo(2,2,2)octyl)-2-(2,3-dicyano-4-ethoxyphenyl)-ethane, 1-(4-pentyl-1-bicyclo(2,2,2)octyl)-2-(2,3-dicyano-4-butoxyphenyl)-ethane, 1-(4-propyl-1-bicyclo(2,2,2)octyl)-2-(2,3-dicyano-4-propanoyloxyphenyl)-ethane, 1-(4-propyl-1-bicyclo(2,2,2)octyl)-2-(2,3-dicyano-4-pentanoyloxyphenyl)-ethane, 1-(4-pentyl-1-bicyclo(2,2,2)octyl)-2-(2,3-dicyano-4-propanoyloxyphenyl)ethane, 1-(4-pentyl-1-bicyclo(2,2,2)octyl)-2-(2,3-dicyano-4-pentanoyloxyphenyl)-ethane, 1-(4-(4-propyl-1-bicyclo(2,2,2)octyl)- phenyl)-2-(2,3-dicyano-4-propylphenyl)-ethane, 1-(4-(4-propyl-1-bicyclo(2,2,2)octyl)phenyl)-2-(2,3-dicyano-4-pentylphenyl)-ethane, 1-(4-(4-pentyl-1-bicyclo(2,2,2)octyl)phenyl)-2-(2,3-dicyano-4-propylphenyl)-ethane, 1-(4-(4-pentyl-1-bicyclo(2,2,2)-octyl)phenyl)-2-(2,3-dicyano-4-pentylphenyl)-ethane, 1-(4-(4-propyl-1-bicyclo(2,2,2)octyl)phenyl)-2-(2,3-dicyano-4-ethoxyphenyl)-ethane, 1-(4-(4-propyl-1-bicyclo(2,2,2)octyl)phenyl)-2-(2,3-dicyano-4-butoxyphenyl)ethane, 1-(4-(4-pentyl-1-bicyclo(2,2,2)octyl)phenyl)-2-(2,3-dicyano-4-ethoxyphenyl)-ethane, 1-(4-(4-pentyl-1-bicyclo(2,2,2)octyl)phenyl)-2-(2,3-dicyano-4-butoxyphenyl)-ethane, 1-(4-propyl-1-bicyclo(2,2,2)octyl)phenyl)-2-(2,3-dicyano-4-propanoyloxyphenyl)-ethane, 1-(4-(propyl-1-bicyclo(2,2,2)octyl)phenyl)-2-(2,3-dicyano-4-pentanoyloxyphenyl)-ethane, 1-(4-(pentyl-1-bicyclo(2,2,2)octyl)phenyl)-2-(2,3-dicyano-4-propanoyloxyphenyl)-ethane, 1-(4-(pentyl-1-bicyclo(2,2,2)octyl)phenyl)-2-(2,3-dicyano-4-pentanoyloxyphenyl)-ethane, 4-propyl-1-bicyclo(2,2,2)-octylmethyl 2,3-dicyano-4-propylphenyl ether, 4-propyl-1-bicyclo(2,2,2)octylmethyl 2,3-dicyano-4-pentylphenyl ether, 4-pentyl-1-bicyclo(2,2,2)octylmethyl 2,3-dicyano-4-propylphenyl ether, 4-pentyl-1-bicyclo(2,2,2)octylmethyl 2,3-dicyano-4-pentylphenyl ether, 1-propyl-4-(2,3-dicyano-4-propylphenyl)-bicyclo(2,2,2)octane, 1-propyl-4-(2,3-dicyano-4-pentylphenyl)-bicyclo(2,2,2)octane, 1-pentyl-4-(2,3-dicyano-4-propylphenyl)-bicyclo(2,2,2)octane, 1-pentyl-4-(2,3-dicyano-4-pentylphenyl)bicyclo(2,2,2)octane, 1-propyl-4-(2,3-dicyano-4-ethoxyphenyl)-bicyclo(2,2,2)octane, 1-propyl-4-(2,3-dicyano-4-butoxyphenyl)-bicyclo(2,2,2)octane, 1-pentyl-4-(2,3-dicyano-4-ethoxyphenyl)-bicyclo(2,2,2)octane, 1-pentyl-4-(2,3-dicyano-4-butoxyphenyl)-bicyclo(2,2,2)octane, 1-propyl-4-(2,3-dicyano-4-propanoyloxyphenyl)-bicyclo(2,2,2)octane, 1-propyl-4-(2,3-dicyano-4-pentanoyloxyphenyl)-bicyclo(2,2,2)octane, 1-pentyl-4-(2,3-dicyano-4-propanoyloxyphenyl)-bicyclo(2,2,2)octane, 1-pentyl-4-(2,3-dicyano-4-pentanoyloxyphenyl)-bicyclo(2,2,2)octane, 1-(4-propyl-1-bicyclo(2,2,2)octyl)-4-(2,3-dicyano-4-propylphenyl)-benzene, 1-(4-propyl-1-bicyclo(2,2,2)octyl)-4-(2,3-dicyano-4-pentylphenyl)-benzene, 1-(4-pentyl-1-bicyclo(2,2,2)octyl)-4-(2,3-dicyano-4-propylphenyl)benzene, 1-(4-pentyl-1-bicyclo(2,2,2)octyl)-4-(2,3-dicyano-4-pentylphenyl)-benzene, 1-(4-propyl-1-bicyclo(2,2,2)octyl)-4-(2,3-dicyano-4-butoxyphenyl)-benzene, 1-(4-pentyl-1-bicyclo(2,2,2)octyl)-4-(2,3-dicyano-4-butoxyphenyl)-benzene, 1-(4-pentyl-1-bicyclo(2,2,2)octyl)-4-(2,3-dicyano-4-propanoyloxyphenyl)-benzene, 1-(4-pentyl-1-bicyclo(2,2,2)octyl)-4-(2,3-dicyano-4-butanoyloxyphenyl)-benzene, 2,3-dicyano-4-propylphenyl 4-(4-propyl-1-bicyclo(2,2,2)octyl)-2-fluorobenzoate, 2,3-dicyano-4-propylphenyl 4-(4-propyl-1-bicyclo(2,2,2)octyl)-2-chlorobenzoate, 2,3-dicyano-4-propylphenyl 4-(4-propyl-1-bicyclo(2,2,2)octyl)-2-bromobenzoate, 2,3-dicyano-4-pentylphenyl 4-(4-pentyl-1-bicyclo(2,2,2)octyl)-3-fluorobenzoate, 2,3-dicyano-4-pentylphenyl 4-(4-pentyl-1-bicyclo(2,2,2)octyl)-3-chlorobenzoate, 2,3-dicyano-4-pentylphenyl 4-(4-pentyl-1-bicyclo(2,2,2)octyl)-3-bromobenzoate, 2,3-dicyano-4-pentylphenyl 4-(4-pentyl-1-bicyclo(2,2,2)octyl)-3-cyanobenzoate, 1-(4-(4-propyl-1-bicyclo(2,2,2)octyl)-2-fluorophenyl)-2-(2,3-dicyano-4-propylphenyl)-ethane, 1-(4-(4-propyl-1-bicyclo(2,2,2)octyl)-2-chlorophenyl)-2-(2,3-dicyano-4-propylphenyl)ethane, 1-(4-(4-propyl-1-bicyclo(2,2,2)octyl)-2-bromophenyl)-2-(2,3-dicyano-4-propylphenyl)-ethane, 1-(4-(4-propyl-1-bicyclo(2,2,2)octyl)-2-fluorophenyl)-2-(2,3-dicyano-4-butoxyphenyl)-ethane, 1-(4-(4-propyl-1-bicyclo(2,2,2)octyl)-2-chlorophenyl)-2-(2,3-dicyano-4-butoxyphenyl)-ethane, 1-(4-(4-propyl-1-bicyclo(2,2,2)octyl)-2-bromophenyl)-2-(2,3-dicyano-4-butoxyphenyl)ethane, 1-(4-(4-propyl-1-bicyclo(2,2,2)octyl)-2-fluorophenyl)-2-(2,3-dicyano-4-propanoyloxyphenyl)-ethane, 1-(4-(4-propyl-1-bicyclo(2,2,2)octyl)-2-chlorophenyl)-2-(2,3-dicyano-4-propanoyloxyphenyl)-ethane, 1-(4-(4-propyl-1-bicyclo(2,2,2)octyl)-2-bromophenyl)-2-(2,3-dicyano-4-propanoyloxyphenyl)-ethane, 1-(4-(4-pentyl-1-bicyclo(2,2,2)octyl)-3-fluorophenyl)-2-(2,3-dicyano-4-pentylphenyl)-ethane, 1-(4-(4-pentyl-1-bicyclo(2,2,2)octyl)-3-chlorophenyl)-2-(2,3-dicyano-4-pentylphenyl)-ethane, 1-(4-(4-pentyl-1-bicyclo(2,2,2)octyl)-3-bromophenyl)-2-(2,3-dicyano-4-pentylphenyl)-ethane, 1-(4-(4-pentyl)-1-bicyclo(2,2,2)octyl)-2,3-difluorophenyl)-2-(2,3-dicyano-4-pentylphenyl)-ethane, 1-(4-(4-pentyl-1-bicyclo(2,2,2)octyl)-3-fluorophenyl)-2-(2,3-dicyano-4-butoxyphenyl)-ethane, 1-(4-(4-pentyl-1-bicyclo(2,2,2)-octyl)-3-chlorophenyl)-2-(2,3-dicyano-4-butoxyphenyl)ethane, 1-(4-(4-pentyl-1-bicyclo(2,2,2)octyl)-3-bromophenyl)-2-(2,3-dicyano-4-butoxyphenyl)-ethane, 1-(4-(4-pentyl-1-bicyclo(2,2,2)octyl)-2,3-dichlorophenyl-2-(2,3-dicyano-4-butoxyphenyl)-ethane, 1-(4-(4-pentyl-1-bicyclo(2,2,2)octyl)-3-fluorophenyl)-2-(2,3-dicyano-4-propanoyloxyphenyl)-ethane, 1-(4-(4-pentyl-1-bicyclo(2,2,2)octyl)-3-chlorophenyl)-2-(2,3-dicyano-4-propanoyloxyphenyl)-ethane, 1-(4-(4-pentyl-1-bicyclo(2,2,2)octyl)-3-bromophenyl)-2-(2,3-dicyano-4-propanoyloxyphenyl)ethane, 1-(4-(4-pentyl-1-bicyclo(2,2,2)octyl)-3-cyanophenyl)-2-(2,3-dicyano-4-propanoyloxyphenyl)-ethane, 1-(4-propyl-1-bicyclo(2,2,2)octyl)-4-(2,3-dicyano-4-propylphenyl)-3-fluorobenzene, 1-(4-propyl-1-bicyclo(2,2,2)octyl)-4-(2,3-dicyano-4-propylphenyl)-3-chlorobenzene, 1-(4-propyl-1-bicyclo(2,2,2)octyl)-4-(2,3-dicyano-4-propylphenyl)-3-bromobenzene, 1-(4-propyl-1-bicyclo(2,2,2)octyl)-4-(2,3-dicyano-4-propylphenyl)-2,3-dicyanobenzene, 1-(4-propyl-1-bicyclo(2,2,2)octyl)-4-(2,3-dicyano-4-butoxyphenyl)-3-fluorobenzene, 1-(4-propyl-1-bicyclo(2,2,2)octyl)-4-(2,3-dicyano-4-butoxyphenyl)-3-chlorobenzene, 1-(4-propyl-1-bicyclo(2,2,2)octyl)-4-(2,3-dicyano-4-butoxyphenyl)-3-bromobenzene, 1-(4-propyl-1-bicyclo(2,2,2)octyl)-4-(2,3-dicyano-4-butoxyphenyl)-2,3-dicyanobenzene, 1-(4-propyl-1-bicyclo(2,2,2)octyl)-4-(2,3-dicyano-4-propanoyloxyphenyl)-3-fluorobenzene, 1-(4-propyl-1-bicyclo(2,2,2)octyl)-4-(2,3-dicyano-4-propanoyloxyphenyl)-3-chlorobenzene, 1-(4-propyl-1-bicyclo(2,2,2)octyl)-4-(2,3-dicyano-4-propanoyloxyphenyl)-3bromobenzene, 1-(4-propyl-1-bicyclo(2,2,2)octyl)-4-(2,3-dicyano-4-propanoyloxyphenyl)-2,3-dicyanobenzene, 1-(4-pentyl-1-bicyclo(2,2,2)octyl)-4-(2,3-dicyano-4-pentylphenyl)-2-fluorobenzene, 1-(4-pentyl-1-bicyclo(2,2,2)-octyl)-4-(2,3-dicyano-4-pentylphenyl)-2-chlorobenzene, 1-(4-pentyl-1-bicyclo(2,2,2)octyl)-4-(2,3-dicyano-4-pentylphenyl)-2-bromobenzene, 1-(4-pentyl-1-bicyclo(2,2,2)octyl)-4-(2,3-dicyano-4-pentylphenyl)-2,3-difluorobenzene, 1-(4-pentyl-1-bicyclo(2,2,2)octyl)-4-(2,3-dicyano-4-butoxyphenyl)-2-fluorobenzene, 1-(4-pentyl-1-bicyclo(2,2,2)octyl)-4-(2,3-dicyano-4-butoxyphenyl)-2-chlorobenzene, 1-(4-pentyl-1-bicyclo(2,2,2)octyl)-4-(2,3-dicyano-4-butoxyphenyl)-2-bromobenzene, 1-(4-pentyl-1-bicyclo(2,2,2)octyl)-4-(2,3-dicyano-4-butoxyphenyl)-2,3-dichlorobenzene, 1-(4-pentyl-1-bicyclo(2,2,2)octyl)-4-(2,3-dicyano-4-propanoyloxyphenyl)-2-fluorobenzene, 1-(4-pentyl-1-bicyclo(2,2,2)octyl)-4-(2,3-dicyano-4-propanoyloxyphenyl)-2-chlorobenzene, 1-(4-pentyl-1- bicyclo(2,2,2)octyl)-4-(2,3-dicyano-4-propanoyloxyphenyl)-2-bromobenzene, 1-(4-pentyl-1-bicyclo(2,2,2)octyl)-4-(2,3-dicyano-4-propanoyloxyphenyl)-2,3-dibromobenzene, 1-(2,3-dicyano-4-propylphenyl) 4-(4-propyl-1-bicyclo(2,2,2)octyl)-2,3-dicyanobenzoate, 1-(2,3-dicyano-4-pentylphenyl) 4-(4-propyl-1-bicyclo(2,2,2)octyl)-2,3-dicyanobenzoate, 1-(2,3-dicyano-4-propylphenyl) 4-(4-pentyl-1-bicyclo(2,2,2)octyl)-2,3-dicyanobenzoate, 1-(2,3-dicyano-4-pentylphenyl) 4-(4-pentyl-1-bicyclo(2,2,2)octyl)-2,3-dicyanobenzoate, 1-[4-(4-propyl-1-bicyclo(2,2,2)octyl)-2,3-dicyanophenyl]-2-(2,3-dicyano-4-propylphenyl)-ethane, 1-[4-(4-propyl-1-bicyclo(2,2,2)octyl)-2,3-dicyanophenyl]-2-(2,3-dicyano-4-pentylphenyl)-ethane, 1-[4-(4-propyl-1-bicyclo(2,2,2)octyl)-2,3-dicyanophenyl]-2-(4-butoxy-2,3-dicyanophenyl)ethane, 1-[4-(4-propyl-1-bicyclo(2,2,2)octyl)-2,3-dicyanophenyl]-2-(4-propanoyloxy-2,3-dicyanophenyl)-ethane, 1-[4-(4-pentyl-1-bicyclo(2,2,2)octyl)-2,3-dicyanophenyl]-2-(2,3-dicyano-4-propylphenyl)-ethane, 1-[4-(4-pentyl-1-bicyclo(2,2,2)octyl)-2,3-dicyanophenyl]-2-(2,3-dicyano-4-pentylphenyl)-ethane, 1-[4-(4-pentyl-1-bicyclo(2,2,2)octyl)-2,3-dicyanophenyl]-2-(4-butoxy-2,3-dicyanophenyl)ethane, 1-[4-(4-pentyl-1-bicyclo(2,2,2)octyl)-2,3-dicyanophenyl]-2-(4-propanoyloxy-2,3-dicyanophenyl)-ethane, 4-(4-propyl-1-bicyclo(2,2,2)octyl)-2,3-dicyano-4'-propylbiphenyl, 4-(4-pentyl-1-bicyclo(2,2,2)octyl)-2,3-dicyano-4'-propylbiphenyl, 4-(4-propyl-1-bicyclo(2,2,2)octyl)-2,3-dicyano-4'-pentylbiphenyl, 4-(4-pentyl-1-bicyclo(2,2,2)octyl)-2,3-dicyano-4'-pentylbiphenyl, 4-(4-propyl-1-bicyclo(2,2,2)octyl)-2,3-dicyano-4'-butoxybiphenyl, 4-(4-pentyl-1-bicyclo(2,2,2)octyl)-2,3-dicyano-4'-butoxybiphenyl, 2'-[4-(4-propyl-1-bicyclo(2,2,2)octyl)-2,3-dicyano-biphenyl]butanoate, 4'-[4-(4-pentyl-1-bicyclo(2,2,2)octyl)-2,3-dicyano-biphenyl]butanoate, 4-(4-propyl-1-bicyclo(2,2,2)octyl)-2,3-dicyano-3'-fluoro-4'-propyl-biphenyl, 4-(4-pentyl-1-bicyclo(2,2,2)octyl)-2,3-dicyano-3'-fluoro-4'-propyl-biphenyl, 4-(4-propyl-1-bicyclo(2,2,2)octyl)-2,3-dicyano-3'-fluoro-4'-pentyl-biphenyl, 4-(4-pentyl-1-bicyclo(2,2,2)octyl)-2,3-dicyano-3'-fluoro-4'-pentyl-biphenyl, 4-(4-propyl-1-bicyclo(2,2,2)-octyl)-2,3-dicyano-4'-butoxy-3'-fluoro-biphenyl, 4-(4-pentyl-1-bicyclo(2,2,2)octyl)-2,3-dicyano-4'-butoxy-3'-fluoro-biphenyl, 4'-[4-(4-propyl-1-bicyclo(2,2,2)octyl)-2,3-dicyano-3'-fluoro-biphenyl]-butanoate, 4'-[4-(4-pentyl-1-bicyclo(2,2,2)octyl)-2,3-dicyano-3'-fluorobiphenyl]butanoate, 4-(4-propyl-1-bicyclo(2,2,2)octyl)2,3-dicyano-3'-chloro-4'-propyl-biphenyl, 4-(4-pentyl-1-bicyclo(2,2,2)octyl)-2,3-dicyano-3'-chloro-4'-propyl-biphenyl, 4-(4-propyl-1-bicyclo(2,2,2)octyl)-2,3-dicyano3'-chloro-4'-pentyl-biphenyl, 4-(4-pentyl-1-bicyclo(2,2,2)-octyl)-2,3-dicyano-4'-chloro-4'-pentyl-biphenyl, 4-(4-propyl-1-bicyclo(2,2,2)octyl)-2,3-dicyano-4'-butoxy-3'-chloro-biphenyl, 4-(4-pentyl-1-bicyclo(2,2,2)octyl)-2,3-dicyano-4'-butoxy-3'-chloro-biphenyl, 4'-[4-(4-propyl-1-bicyclo(2,2,2)octyl)-2,3-dicyano-3'-chloro-biphenyl]-butanoate, 4'-[4-(4-pentyl-1-bicyclo(2,2,2)octyl)-2,3-dicyano-3'-chloro-biphenyl]butanoate, 4-(4-propyl-1-bicyclo(2,2,2)octyl)-2,3-dicyano-3'-bromo-4'-propyl-biphenyl, 4-(4-propyl-1-bicyclo(2,2,2)octyl)-2,3-dicyano-3'-bromo-4'-pentyl-biphenyl, 4-(4-propyl-1-bicyclo(2,2,2)octyl)-2,3-dicyano-3'-bromo-4'-butoxy-biphenyl, 4-(4-pentyl-1-bicyclo(2,2,2)octyl)-2,3-dicyano-3'-bromo-4'-propyl-biphenyl, 4-(4-pentyl-1-bicyclo(2,2,2)octyl)-2,3-dicyano-3'-bromo-4'-pentyl-biphenyl, 4-(4-pentyl-1-bicyclo(2,2,2)octyl)-2,3-dicyano-3'-bromo-4'-butoxy-biphenyl, 4'-[4-(4-propyl-1-bicyclo(2,2,2)octyl)-2,3-dicyano-3'-bromo-biphenylyl]butanoate, 4'-[4-(4-pentyl-1-bicyclo(2,2,2)octyl)-2,3-dicyano-3'-bromo-biphenylyl]butanoate, 4-(4-propyl-1-bicyclo(2,2,2)octyl)-2,3-dicyano4'-butoxy-3'-cyano-biphenyl, 4-(4-propyl-1-bicyclo(2,2,2)octyl)-2,3-dicyano-3'-cyano-4'-propyl-biphenyl, 4-(4-propyl-1-bicyclo(2,2,2)octyl)-2,3-dicyano-3'-cyano-4'-pentyl-biphenyl, 4-(4-pentyl-1-bicyclo(2,2,2)octyl)-2,3-dicyano-4'-butoxy-3'-cyano-biphenyl, 4-(4-pentyl-1-bicyclo(2,2,2)octyl)-2,3-dicyano-3'-cyano-4'-propyl-biphenyl, 4-(4-pentyl-1-bicyclo(2,2,2)octyl)-2,3-dicyano-3'-cyano-4'-pentyl-biphenyl, 4'-[4-(4-propyl-1-bicyclo(2,2,2)octyl)-2,3-dicyano-3'-cyano-biphenylyl]-butanoate, 4'-[4-(4-pentyl-1-bicyclo(2,2,2)octyl)-2,3-dicyano-3'-cyanobiphenylyl]butanoate, 1-[4-(4-propyl-1-bicyclo(2,2,2)octyl)-2,3-dicyanophenyl]-2-(4-propylphenyl)-ethane, 1-[4-(4-propyl-1-bicyclo(2,2,2)octyl)-2,3-dicyanophenyl]-2-(4-pentylphenyl)-ethane, 1-[4-(4-propyl-1-bicyclo(2,2,2)-octyl)-2,3-dicyanophenyl]-2-(4-butoxyphenyl)-ethane, 1-[4-(4-propyl-1-bicyclo(2,2,2)octyl)-2,3-dicyanophenyl]-2-(4-propylcarbonyloxyphenyl)-ethane, 1-[4-(4-pentyl-1-bicyclo(2,2,2)octyl)-2,3-dicyanophenyl]-2-(4-propylphenyl)ethane, 1-[4-(4-pentyl-1-bicyclo(2,2,2)octyl)-2,3-dicyanophenyl]-2-(4-pentylphenyl)-ethane, 1-[4-(4-pentyl-1-bicyclo(2,2,2)octyl)-2,3-dicyanophenyl]-2-(4-butoxyphenyl)ethane, 1-[4-(4-pentyl-1-bicyclo(2,2,2)octyl)-2,3-dicyanophenyl]-2-(4-propanoyloxyphenyl)-ethane, 1-[4-(4-propyl-1-bicyclo(2,2,2)octyl)-2,3-dicyanophenyl]-2-(3-fluoro-4-propylphenyl)-ethane, 1-[4-(4-propyl-1-bicyclo(2,2,2)octyl)-2,3-dicyanophenyl]-2-(3-fluoro-4-pentylphenyl)ethane, 1-[4-(4-propyl-1-bicyclo(2,2,2)octyl)-2,3-dicyanophenyl]-2-(4-butoxy-3-fluorophenyl)-ethane, 1-[4-(4-propyl-1-bicyclo(2,2,2)octyl)-2,3-dicyanophenyl]-2-(3-fluoro-4-propanoyloxyphenyl)-ethane, 1-[4-(4-pentyl-1-bicyclo(2,2,2)octyl)-2,3-dicyanophenyl]-2-(3-fluoro-4-propylphenyl)-ethane, 1-[4-(4-pentyl-1-bicyclo(2,2,2)octyl)-2,3-dicyanophenyl]-2-(3-fluoro-4-pentylphenyl)-ethane, 1-[4-(4-pentyl-1-bicyclo(2,2,2)octyl)-2,3-dicyanophenyl]-2-(4-butoxy-3-fluorophenyl)-ethane, 1-[4-(4-pentyl-1-bicyclo(2,2,2)octyl)-2,3-dicyanophenyl]-2-(3-fluoro-4-propanoyloxyphenyl)-ethane, 1-[4-(4-propyl-1-bicyclo(2,2,2)octyl)-2,3-dicyanophenyl]-2-(3-chloro-4-propylphenyl)-ethane, 1-[4-(4-propyl-1-bicyclo(2,2,2)octyl)-2,3-dicyanophenyl]-2-(3-bromo-4-pentylphenyl)-ethane, 1-[4-(4-propyl-1-bicyclo(2,2,2)octyl)-2,3-dicyanophenyl]-2-(4-butoxy-3-chlorophenyl)-ethane, 1-[4-(4-propyl-1-bicyclo(2,2,2)octyl)-2,3-dicyanophenyl]-2-(3-chloro-4-propanoyloxyphenyl)-ethane, 1-[4-(4-pentyl-1-bicyclo(2,2,2)octyl)-2,3-dicyanophenyl]-2-(3-chloro-4-propylphenyl)-ethane, 1-[4-(4-pentyl-1-bicyclo(2,2,2)octyl)- 2,3-dicyanophenyl]-2-(3-chloro-4-pentylphenyl)-ethane, 1-[4-(4-pentyl-1-bicyclo(2,2,2)octyl)-2,3-dicyanophenyl]-2-(4-butoxy-3-chlorophenyl)-ethane, 1-[4-(4-pentyl-1-bicyclo(2,2,2)octyl)-2,3-dicyanophenyl]-2-(3-chloro-4-propanoyloxyphenyl)-ethane, 1-[4-(4-propyl-1-bicyclo(2,2,2)octyl)-2,3-dicyanophenyl]-2-(3-bromo-4-propylphenyl)-ethane, 1-[4-(4-propyl-1-bicyclo(2,2,2)octyl)-2,3-dicyanophenyl]-2-(3-bromo-4-pentylphenyl)-ethane, 1-[4-(4-propyl-1-bicyclo(2,2,2)octyl)-2,3-dicyanophenyl]-2-(3-bromo-4-butoxyphenyl)-ethane, 1-[4-(4-propyl-1-bicyclo(2,2,2)octyl)-2,3-dicyanophenyl]-2-(3-bromo-4-propanoyloxyphenyl)-ethane, 1-[4-(4-pentyl-1-bicyclo(2,2,2)octyl)-2,3-dicyanophenyl]-2-(3-bromo-4-propylphenyl)-ethane, 1-[4-(4-pentyl-1-bicyclo(2,2,2)octyl)-2,3-dicyanophenyl]-2-(3-bromo-4-pentylphenyl)-ethane, 1-[4-(4-pentyl-1-bicyclo(2,2,2)octyl)-2,3-dicyanophenyl]-2-(3-bromo-4-butoxyphenyl)ethane, 1-[4-(4-pentyl-1-bicyclo(2,2,2)octyl)-2,3-dicyanophenyl]-2-(3-bromo-4-propanoyloxyphenyl)-ethane, 1-[4-(4-propyl-1-bicyclo(2,2,2)octyl)-2,3-dicyanophenyl]-2-(3-cyano-4-propylphenyl)-ethane, 1-[4-(4-propyl-1-bicyclo(2,2,2)octyl)-2,3-dicyanophenyl]-2-(3-cyano-4-pentylphenyl)-ethane, 1-[4-(4-propyl-1-bicyclo(2,2,2)octyl)-2,3-dicyanophenyl]-2-(4-butoxy-3-cyanophenyl)-ethane, 1-[4-(4-propyl-1-bicyclo(2,2,2)octyl)-2,3-dicyanophenyl]-2-(3-cyano-4-propanoyloxyphenyl)-ethane, 1-[4-(4-pentyl-1-bicyclo(2,2,2)octyl)-2,3-dicyanophenyl]-2-(3-cyano-4-propylphenyl)-ethane, 1-[4-(4-pentyl-1-bicyclo(2,2,2)octyl)-2,3-dicyanophenyl]-2-(3-cyano-4-pentylphenyl)ethane, 1-[4-(4-pentyl-1-bicyclo(2,2,2)octyl)-2,3-dicyanophenyl]-2-(4-butoxy-3-cyanophenyl)-ethane, 1-[4-(4-pentyl-1-bicyclo(2,2,2)octyl)-2,3-dicyanophenyl]-2-(3-cyano-4-propanoyloxyphenyl)-ethane, 1-[4-(4-propyl-1-bicyclo(2,2,2)octyl)-2,3dicyanophenyl]-2-(2-fluoro-4-propylphenyl)-ethane, 1-[4-(4-propyl-1-bicyclo(2,2,2)octyl)-2,3-dicyanophenyl]-2-(2-fluoro-4-pentylphenyl)-ethane, 1-[4-(4-propyl-1-bicyclo(2,2,2)octyl)-2,3-dicyanophenyl]-2-(4-butoxy-2-fluorophenyl)-ethane, 1-[4-(4-propyl-1-bicyclo(2,2,2)octyl)-2,3-dicyanophenyl]-2-(2-fluoro-4-propanoyloxyphenyl)-ethane, 1-[4-(4-pentyl-1-bicyclo-(2,2,2)octyl)-2,3-dicyanophenyl]-2-(2-fluoro-4-propylphenyl)-ethane, 1-[4-(4-pentyl-1-bicyclo(2,2,2)octyl)-2,3-dicyanophenyl]-2-(2-fluoro-4-pentylphenyl)-ethane, 1-[4-4-(4-pentyl-1-bicyclo(2,2,2)octyl)-2,3-dicyanophenyl]-2-(4-butoxy-2-fluorophenyl)-ethane, 1-[4-(4-pentyl-1-bicyclo(2,2,2)octyl)-2,3-dicyanophenyl]-2-(2-fluoro-4-propanoyloxyphenyl)-ethane, 1-[4-(4-propyl-1-bicyclo(2,2,2)octyl)-2,3-dicyanophenyl]-2-(2-chloro-4-propylphenyl)-ethane, 1-[4-(4-propyl-1-bicyclo(2,2,2)octyl)-2,3-dicyanophenyl]-2-(2-chloro-4-pentylphenyl)-ethane, 1-[4-(4-propyl-1-bicyclo(2,2,2)octyl)-2,3-dicyanophenyl]-2-(2-butoxy-2-chlorophenyl)-ethane, 1-[4-(4-propyl-1-bicyclo(2,2,2)octyl)-2,3-dicyanophenyl]-2-(2-chloro-4-propanoyloxyphenyl)-ethane, 1-[4-(4-pentyl-1-bicyclo(2,2,2)-octyl)-2,3-dicyanophenyl]-2-(2-chloro-4-propylphenyl)-ethane, 1-[4-(4-pentyl-1-bicyclo(2,2,2)octyl)-2,3-dicyanophenyl]-2-(2-chloro-4-pentylphenyl)-ethane, 1-[4-(4-pentyl-1-bicyclo(2,2,2)octyl)-2,3-dicyanophenyl]-2-(2-butoxy-2-chlorophenyl)-ethane, 1-[4-(4-pentyl-1-bicyclo(2,2,2)octyl)-2,3-dicyanophenyl]-2-(2-chloro-4-propanoyloxyphenyl)-ethane, 1-[4-(4-propyl-1-bicyclo(2,2,2)octyl)-2,3-dicyanophenyl]-2-(2-bromo-4-propylphenyl)-ethane, 1-[4-(4-propyl-1-bicyclo(2,2,2)octyl)-2,3-dicyanophenyl]-2-(2-bromo-4-pentylphenyl)-ethane, 1-[4-(4-propyl-1-bicyclo(2,2,2)octyl)-2,3-dicyanophenyl]-2-(2-bromo-4-butoxyphenyl)-ethane, 1-[4-(4-propyl-1-bicyclo(2,2,2)octyl)-2,3-dicyanophenyl]-1-(2-bromo-4-propanoyloxyphenyl)-ethane, 1-[4-(4-pentyl-1-bicyclo(2,2,2)octyl)-2,3-dicyanophenyl]-2-(2-bromo-4-propylphenyl)ethane, 1-[4-(4-pentyl-1-bicyclo(2,2,2)octyl)-2,3-dicyanophenyl]2-(2-bromo-4-pentylphenyl)-ethane, 1-]4-(4-pentyl-1-bicyclo(2,2,2)octyl)-2,3-dicyanophenyl]-2-(2-bromo-4-butoxyphenyl)-ethane, 1-[4-(4-pentyl-1-bicyclo(2,2,2)-octyl)-2,3-dicyanophenyl]1-(2-bromo-4-propanoyloxyphenyl)-ethane, 1-[4-(4-propyl-1-bicyclo(2,2,2)octyl)-2,3-dicyanophenyl]-2-(2-cyano-4-propylphenyl)-ethane, 1-[4-(4-propyl-1-bicyclo(2,2,2)octyl)-2,3-dicyanophenyl]-2-(2-cyano-4-pentylphenyl)-ethane, 1-[4-(4-propyl-1-bicyclo(2,2,2)-octyl)-2,3-dicyanophenyl]-2-(4-butoxy-2-cyanophenyl)ethane, 1-[4-(4-propyl-1-bicyclo(2,2,2)octyl)-2,3-dicyanophenyl]-2-(2-cyano-4-propanoyloxyphenyl)-ethane, 1-[4-(4-pentyl-1-bicyclo(2,2,2)octyl)-2,3-dicyanophenyl]-2-(2-cyano-4-propylphenyl)-ethane, 1-[4-(4-pentyl-1-bicyclo(2,2,2)octyl)-2,3-dicyanophenyl]-2-(2-cyano-4-pentylphenyl)-ethane, 1-[4-(4-pentyl-1-bicyclo(2,2,2)octyl)-2,3-dicyanophenyl]-2-(4-butoxy-2-cyanophenyl)-ethane, 1-[4-(4-pentyl-1-bicyclo(2,2,2)octyl)-2,3-dicyanophenyl]-2-(2-cyano-4-propanoyloxyphenyl)-ethane, 1-(4-propyl-1-bicyclo(2,2,2)octyl)-2,3-dicyano-4-(trans-4-propylcyclohexyl)-benzene, 1-(4-propyl-1-bicyclo(2,2,2)octyl)-2,3-dicyano-4-(trans-4-pentylcyclohexyl)-benzene, 1-(4-pentyl-1-bicyclo(2,2,2)octyl)-2,3-dicyano-4-(trans-4-propylcyclohexyl)-benzene, 1-(4-pentyl-1-bicyclo(2,2,2)octyl)-2,3-dicyano-4-(trans-4-pentylcyclohexyl)-benzene, 1-[4-(4-propyl-1-bicyclo(2,2,2)octyl)-2,3-dicyanophenyl]-2-(trans-4-propylcyclohexyl)-ethane, 1-[4-(4-propyl-1-bicyclo(2,2,2)octyl)-2,3-dicyanophenyl]-2-(trans-4-pentylcyclohexyl)-ethane, 1-[4-(4-pentyl-1-bicyclo(2,2,2)octyl)-2,3-dicyanophenyl]-2-(trans-4-propylcyclohexyl)-ethane, 1-[4-(4-pentyl-1-bicyclo(2,2,2)octyl)-2,3-dicyanophenyl]-2-(trans-4-pentylcyclohexyl)-ethane, 4-(4-propyl-1-bicyclo(2,2,2)octyl) 2,3-dicyanophenyl-trans-4-propylcyclohexane-1-carboxylate, 4-(4-propyl-1-bicyclo(2,2,2)octyl) 2,3-dicyanophenyl-trans-4-pentylcyclohexane-1-carboxylate, 4-(4-pentyl-1-bicyclo(2,2,2)octyl) 2,3-dicyanophenyl-trans-4-propylcyclohexane-1-carboxylate, 4-(4-pentyl-1-bicyclo(2,2,2)octyl) 2,3-dicyanophenyl-trans-4-pentylcyclohexane-1-carboxylate, 1,4-bis(4-propyl-1-bicyclo(2,2,2)octyl)-2,3-dicyano-benzene, 1,4-bis(4-pentyl-1-bicyclo(2,2,2)octyl)-2,3-dicyano-benzene, 1-(4-pentyl-1-bicyclo(2,2,2)octyl)-4-(4-propyl-1-bicyclo(2,2,2)octyl)-2,3-dicyano-benzene, 1-[4-(4-propyl-1-bicyclo(2,2,2)octyl)-2,3-dicyanophenyl]-2-(4-propyl-1-bicyclo(2,2,2)octyl)-ethane, 1-[4-(4-propyl-1-bicyclo(2,2,2)octyl)-2,3-dicyanophenyl]-2-(4-pentyl-1-bicyclo(2,2,2)octyl)ethane, 1-[4-(4-pentyl-1-bicyclo(2,2,2)octyl)-2,3-dicyanophenyl]-2-(4-propyl-1-bicyclo(2,2,2)octyl)-ethane, 1-[4-(4-pentyl-1-bicyclo(2,2,2)octyl)-2,3-dicyanophenyl]-2-(4-pentyl-1-bicyclo(2,2,2)octyl)-ethane, 4-(4-propyl-1-bicyclo(2,2,2)octyl)2,3-dicyanophenyl-4-propylbicyclo(2,2,2)octane-1-carboxylate, 4-(4-propyl-1-bicyclo(2,2,2)octyl) 2,3-dicyanophenyl-4-pentylbicyclo(2,2,2)octane-1-carboxylate, 4-(4-pentyl-1-bicyclo(2,2,2)octyl) 2,3-dicyanophenyl-4-propylbicyclo(2,2,2)octane-1-carboxylate, 4-(4-pentyl-1-bicyclo(2,2,2)octyl)-2,3-dicyanophenyl-4-pentylbicyclo(2,2,2)octane-1-carboxylate, 1-(4-propyl-1-bicyclo(2,2,2)octyl)-2,3-dicyano-4-(4-propyl-1-bicyclo(2,2,2)octyl)-methoxy-benzene, 1-(4-propyl-1-bicyclo(2,2,2)octyl)-2,3-dicyano-4-(4-pentyl-1-bicyclo(2,2,2)octyl)-methoxy-benzene, 1-(4-pentyl-1-bicyclo(2,2,2)octyl)-2,3-dicyano-4-(4-propyl-1-bicyclo(2,2,2)octyl)-methoxybenzene, 1-(4-pentyl-1-bicyclo(2,2,2)octyl)-2,3-dicyano-4-(4-pentyl-1-bicyclo(2,2,2)octyl)-methoxy-benzene, 4-(4-propyl-1-bicyclo(2,2,2)octyl)-methoxy-2,3-dicyano-4'-propyl-biphenyl, 4-(4-propyl-1-bicyclo(2,2,2)octyl)-methoxy-2,3-dicyano-4'-pentyl-biphenyl, 4-(4-propyl-1-bicyclo(2,2,2)octyl)-methoxy-2,3-dicyano-4'-butoxy-biphenyl, 4-(4-propyl-1-bicyclo(2,2,2)octyl)-methoxy-2,3-dicyano-4'-propanoyloxy-biphenyl, 4-(4-pentyl-1-bicyclo(2,2,2)octyl)-methoxy-2,3-dicyano-4'-propyl-biphenyl, 4-(4-pentyl-1-bicyclo(2,2,2)octyl)-methoxy-2,3-dicyano-4'-butoxy-biphenyl, 4-(4- pentyl-1-bicyclo(2,2,2)octyl)-methoxy-2,3-dicyano-4'-propanoyloxy-biphenyl, 4-[2-(4-propyl-1-bicyclo(2,2,2)octyl)-ethyl]-2,3-dicyano-4'-propyl-biphenyl, 4-[2-(4-propyl-1-bicyclo(2,2,2)octyl)-ethyl]-2,3-dicyano-4,-pentyl-biphenyl, 4-[2-(4-propyl-1-bicyclo(2,2,2)octyl)-ethyl]-2,3-dicyano-4'-butoxy-biphenyl, 4-[2-(4-propyl-1-bicyclo(2,2,2)octyl)-ethyl]-2,3-dicyano-4'-propanoyloxy-biphenyl, 4-[2-(4-pentyl-1-bicyclo(2,2,2)octyl)-ethyl]-2,3-dicyano-4'-propyl-biphenyl, 4-[2-(4-pentyl-1-bicyclo(2,2,2)octyl)-ethyl]-2,3-dicyano-4'-pentyl-biphenyl, 4-[2-(4-pentyl-1-bicyclo(2,2,2)octyl)ethyl]-2,3-dicyano-4'-butoxy-biphenyl, 4-[2-(4-pentyl-1-bicyclo(2,2,2)octyl)-ethyl]-2,3-dicyano-4'-propanoyloxy-biphenyl, 4-(2,3-dicyano-4'-propyl-biphenylyl) 4-propyl-bicyclo(2,2,2)octane-1-carboxylate, 4-(2,3-dicyano-4'-pentyl-biphenylyl) 4-propyl-bicyclo(2,2,2)octane-1-carboxylate, 4-(4'-butoxy-2,3-dicyano-biphenylyl) 4-propylbicyclo(2,2,2)octane-1-carboxylate, 4-(4'-butanoyloxy-2,3-dicyano-biphenylyl) 4-propyl-bicyclo(2,2,2)octane-1-carboxylate, 4-(2,3-dicyano-4'-propyl-biphenylyl) 4-pentylbicyclo(2,2,2)octane-1-carboxylate, 4-(2,3-dicyano-4'-pentyl-biphenylyl) 4-pentyl-bicyclo(2,2,2)octane-1-carboxylate, 4-(4'-butoxy-2,3-dicyano-biphenylyl) 4-pentylbicyclo(2,2,2)octane-1-carboxylate, 4-(4'-butanoyloxy-2,3-dicyano-biphenylyl) 4-pentyl-bicyclo(2,2,2)octane-1-carboxylate, 1-(4-propyl-1-bicyclo(2,2,2)octyl)-methoxy-2,3-dicyano-4-(trans-4-propylcyclohexyl)-benzene, 1-(4-propyl-1-bicyclo(2,2,2)octyl)-methoxy-2,3-dicyano-4-(trans-4-pentylcyclohexyl)-benzene, 1-(4-pentyl-1-bicyclo(2,2,2)octyl)-methoxy-2,3-dicyano-4-(trans-4-propylcyclohexyl)benzene, 1-(4-pentyl-1-bicyclo(2,2,2)octyl)-methoxy-2,3-dicyano-4-(trans-4-pentylcyclohexyl)-benzene, 2,3-dicyano-1-(trans-4-propylcyclohexyl)-4-(2-(4-propyl-1-bicyclo(2,2,2)octyl)-ethyl-benzene, 2,3-dicyano-1-(trans-4-pentylcyclohexyl)-4-(2-(4-propyl-1-bicyclo(2,2,2)octyl)ethyl-benzene, 2,3-dicyano-1-(trans-4-propylcyclohexyl)-4-(2-(4-pentyl-1-bicyclo(2,2,2)octyl)-ethyl-benzene, 2,3-dicyano-1-(trans-4-pentylcyclohexyl)-4-(2-(4-pentyl-1-bicyclo(2,2,2)octyl)-ethyl-benzene, 1-[2,3-dicyano-4-(trans-4-propylcyclohexyl)]-phenyl 4-propyl-bicyclo(2,2,2)octane-1-carboxylate, 1-[2,3-dicyano-4-(trans-4-pentylcyclohexyl)]-phenyl 4-propyl-bicyclo(2,2,2)octane-1-carboxylate, 1-[2,3-dicyano-4-(trans-4-propylcyclohexyl)]-phenyl 4-pentyl-bicyclo(2,2,2)octane-1-carboxylate and 1-[2,3-dicyano-4-(trans-4-pentylcyclohexyl)]-phenyl 4-pentyl-bicyclo(2,2,2)octane-1-carboxylate.

We claim:

1. An anisotropic compound having a negative DC anistropy and improved photochemical stability of the formula

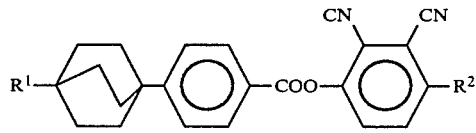

wherein $R^1$ and $R^2$ each are alkyl with in each case 1 to 12 C-atoms in a straight or branched chain, which may be chiral.

2. An anisotropic compound according to claim 1, which is 2,3-dicyano-4-pentylphenyl 4-(4pentyl-1-bicyclo(2,2,2)octyl)-benzoate.

3. A liquid crystal mixture which contains at least one anisotropic compound according to claim 1.

4. A liquid crystal mixture which contains at least one anisotropic compound as claimed in claim 1.

* * * * *